United States Patent
Mongrenier

(10) Patent No.: US 10,733,399 B2
(45) Date of Patent: *Aug. 4, 2020

(54) METHOD FOR CARRYING OUT AN INVENTORY OF A PLURALITY OF BIOLOGICAL CONTAINERS AND ASSOCIATED GANTRY

(71) Applicant: BIOLOG-ID, Boulogne-Billancourt (FR)

(72) Inventor: Jean-Claude Mongrenier, Versailles (FR)

(73) Assignee: BIOLOG-ID, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/666,847

(22) Filed: Oct. 29, 2019

(65) Prior Publication Data
US 2020/0065533 A1 Feb. 27, 2020

Related U.S. Application Data

(62) Division of application No. 16/314,536, filed as application No. PCT/EP2016/075511 on Oct. 24, 2016.

(51) Int. Cl.
*G06K 7/10* (2006.01)
*G16H 10/40* (2018.01)
(Continued)

(52) U.S. Cl.
CPC ......... *G06K 7/10425* (2013.01); *G16H 10/40* (2018.01); *G06Q 10/087* (2013.01); *G16H 40/20* (2018.01)

(58) Field of Classification Search
CPC ............ G06F 19/3462; G06K 7/10366; G06K 7/10425; G16H 20/13; G16H 10/40
See application file for complete search history.

(56) References Cited

U.S. PATENT DOCUMENTS 5,726,630 A 3/1998 Marsh et al.
9,275,262 B2 3/2016 Mongrenier et al.
(Continued)

FOREIGN PATENT DOCUMENTS

| EP | 0 598 624 A1 | 5/1994 |
| EP | 1 693 807 A1 | 8/2006 |
| FR | 2 988 936 A1 | 10/2013 |

OTHER PUBLICATIONS

Cecilia Amador et al: "Application of RFID Technologies in the Temperature Mapping of the Pineapple Supply Chain"; Article in Sensing and Instrumentation for Food Quality and Safety—Mar. 2009, Received: Oct. 1, 2008 / Accepted: Jan. 15, 2009 / Published online: Feb. 4, 2009, Sens. & Instrumen. Food Qual. (2009) 3:26-33.

(Continued)

*Primary Examiner* — Omeed Alizada
(74) *Attorney, Agent, or Firm* — Young & Thompson

(57) ABSTRACT

Disclosed is a method for carrying out an inventory of a plurality of biological product containers, each container and/or each package including containers being provided with an identification label comprising a wireless communication chip. The method includes the steps of: providing a device with a gantry defining a direction of travel; providing a receptacle able to be moved, the receptacle carrying the containers; moving the receptacle in order to cross the gantry in the direction of travel; and reading the wireless communication chip of each container and/or package during the movement of the receptacle.

11 Claims, 2 Drawing Sheets

(51) Int. Cl.
*G16H 40/20* (2018.01)
*G06Q 10/08* (2012.01)

(56) References Cited

U.S. PATENT DOCUMENTS

2008/0203160 A1   8/2008   Lee
2015/0015373 A1   1/2015   Mongrenier et al.

OTHER PUBLICATIONS

Dario Borghino "Intelligent blood bags optimize supplies and prevent dangerous mistakes", Dec. 14, 2009.

John G. Gibson et al.: "The Effect of Varying Temperatures on the Posttransfusion Survival of Whole Blood During Depot Storage and After Transportation by Land and Air 1" Received for publication Aug. 31, 1946, John Gibson, 2nd, Theodore Sack, Robley Evans, and Wendell Peacock.

T.R. Hamill "The 30-minute rule for reissuing blood: are we needlessly discarding units?", Received for publication Sep. 8, 1988; revision received Jul. 6, 1989, and accepted Jul. 9, 1989. 1990—vol. 30. No. 1.

Soo-Jung Kim et al.: "Smart Blood Bag Management System in a Hospital Environment", IFIP International Federation for Information Processing 2006, pp. 506-517, 2006.

Intelligent blood bags, Dec. 1, 2009, Blood bags that are not needed during an operation can only be reused if the cold chain has been maintained. In the future, a radio node attached to the blood bag will constantly monitor the temperature. (© Universitätsklinikum Erlangen).

P. Pick and J. Fabijanic: "Temperature Changes in Donor Blood under Different Storage Conditions", From the Diagnostic Research Department, Hoffmann-La Roche, Inc, Nutley, New Jersey, Jul.-Aug. 1971, vol. 11 No. 4.

Sunita Saxena et al.; "The Risk of Bacterial Growth in Units of Blood that Have Warmed to More Than 10° C.", Received Sep. 1, 1989; received revised manuscript and accepted for publication Nov. 1, 1989, vol. 94 • No. 1.

Sunita Saxena et al.: "A comprehensive assessment program to improve blood-administering practices using the Focus-PDCA model", 1350-1356 Transfusion vol. 44, Sep. 2004.

C. E. Shields, "Studies on Stored Whole Blood", IV. Effects of Temperature and Mechanical Agitation on Blood with and without Plasma, Transfusion, vol. 10, No. 4 Jul.-Aug. 1970.

Blood bags with RFID chips , Secure transport from vein to vein, Jun. 15, 2010.

FR Search Report, dated Mar. 28, 2017, from corresponding FR 1656321 application.

International Search Report, dated Apr. 5, 2017, from corresponding PCT/EP2016/075511 application.

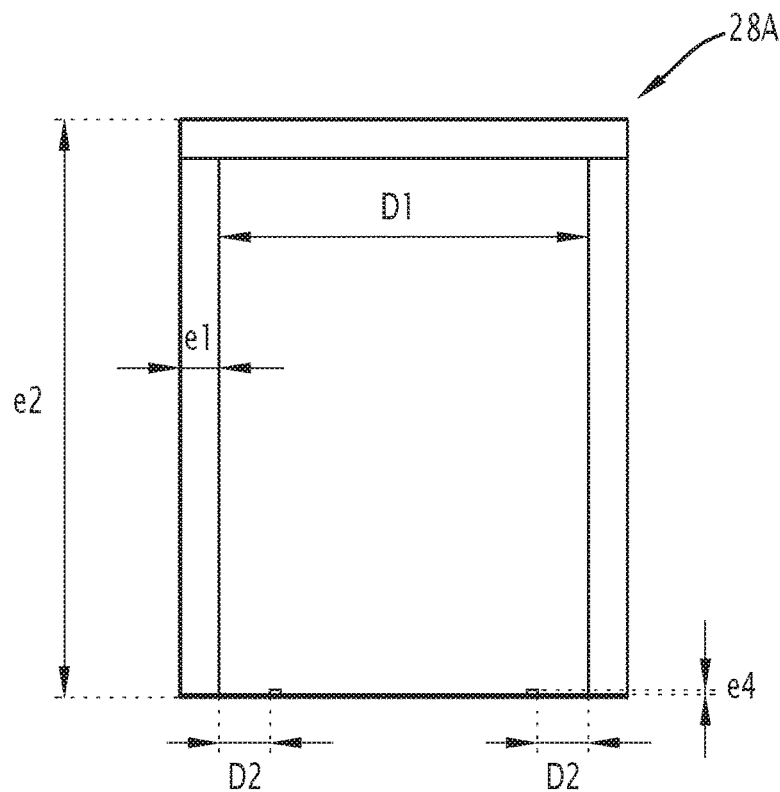
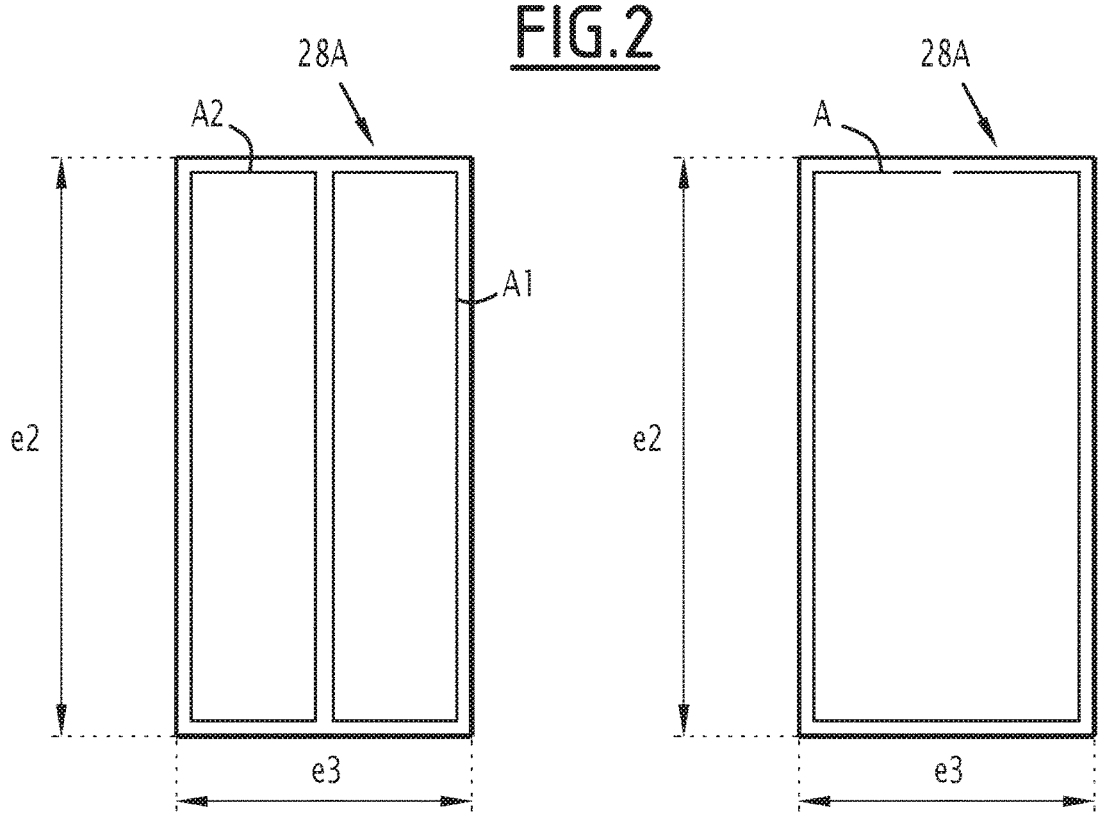

METHOD FOR CARRYING OUT AN INVENTORY OF A PLURALITY OF BIOLOGICAL CONTAINERS AND ASSOCIATED GANTRY

BACKGROUND OF THE INVENTION

Field of the Invention

The present invention relates to a method for carrying out an inventory of a plurality of biological product containers and an RFID gantry for carrying out an inventory of a plurality of biological product containers.

The present invention relates to the field of container logistics.

Description of the Related Art

Such containers are for example pouches containing biological products such as blood products (pouches of primary blood, plasma, platelets, red blood cells, etc.) or cellular engineering products (stem cells, etc.), or drug pouches such as chemotherapy pouches.

All throughout container transport, it is imperative to guarantee minimal exposure of the containers to a relatively high temperature. Thus, for certain biological products, laws require a maximal exposure time of the containers to a temperature greater than $-4°$ C. This maximum time is set in Europe at 2 hours and 30 minutes by the directive.

Furthermore, for profitability reasons, a large number of containers must be handled at one time.

In the case of pouches containing blood products, it is known that the pouches are placed in a refrigerated truck in the form of packages, these packages sometimes being gathered to form assemblies that are easy to unload. The operator then unloads each assembly in a cabinet made from metal grating or a caddy with casters or a pallet carried by pallet truck that the operator pushes to an intermediate chamber at a temperature of $4°$ C. In this intermediate chamber, the operator verifies the presence of each pouch or each set of pouches to perform an inventory by scanning barcodes present on the pouches or on each set of pouches. Sorting is then done, for example, based on the origin or the category of the blood product. Each set of pouches is next reloaded on a pallet. The operator next places the pouches in a cold chamber at about $-40°$ C. in the case of plasma during a so-called quarantine period, the quarantine period being greater than or equal to 60 days. The plasma is then able to be fractionated.

However, the time taken by the operator for one assembly is relatively long, approximately 4 hours to 5 hours, and this time should be reduced to comply with the legal requirements or good practices in order to guarantee a certain quality.

There is there a need for a method for carrying out an inventory of a plurality of biological product containers that is fast to carry out.

BRIEF SUMMARY OF THE INVENTION

According to the invention, this aim is achieved by a method for carrying out an inventory of a plurality of biological product containers, each container and/or each package comprising containers being provided with an identification label with a wireless communication chip, the method comprising the following steps:

providing a device for carrying out an inventory, the device including a gantry defining a direction of travel, the gantry comprising two reading panels, the reading panels each including at least one antenna, the antennas being capable of reading a wireless communication chip, providing a receptacle able to be moved, the receptacle bearing the plurality of containers for which an inventory is to be carried out, moving the receptacle in order to cross the gantry in the direction of travel, and reading, by at least one of the reading panels, the wireless communication chip of each container and/or package during the movement of the receptacle.

According to specific embodiments, the method comprises one or more of the following features, considered alone or according to any technically possible combinations:

the receptacle is at a distance from one of the reading panels smaller than 10 cm during the movement, the gantry includes a floor including at least one guide member extending along the direction of travel, each guide member being associated with a respective reading panel and being arranged at a distance smaller than 20 centimeters from a respective reading panel along a direction transverse to the direction of travel, each receptacle comprising a plurality of casters, at least one caster being provided to cooperate with at least one guide member, the movement and reading steps are carried out in an enclosure with a controlled atmosphere, the receptacle comprises at least one wall formed by a metal grating, the reading panels each include a plurality of antennas capable of reading a wireless communication chip placed next to one another and the reading step is carried out by successive supply of the antennas with current during a predefined period of time, an antenna of a reading panel is associated bijectively with an antenna of another reading panel to form pairs of antennas, the current applied in each pair of antennas respects one of the following conditions: being in phase, being phase-shifted by $90°$ and being phase-shifted by $180°$, each reading panel includes only two antennas, and each reading panel includes only one antenna, the antennas of the reading panels being associated bijectively to form a pair of antennas.

The invention also relates to a device for carrying out an inventory of a plurality of biological product containers, each container and/or each package comprising containers being provided with an identification label with a wireless communication chip, the plurality of containers for which an inventory must be carried out being part of a receptacle, the device comprising:

a gantry defining a direction of travel, the gantry comprising two reading panels, the reading panels each including at least one antenna, the antennas being capable of reading a wireless communication chip, and a control terminal comprising a controller suitable for commanding the antennas to carry out a reading step by at least one of the reading panels of the wireless communication chip of each container and/or package during the movement of the receptacle to traverse the gantry along the direction of travel.

BRIEF DESCRIPTION OF THE DRAWINGS

Other features and advantages of the invention will appear upon reading the following description of embodiments of the invention, provided as an example only and in reference to the drawings, which are.

DETAILED DESCRIPTION OF THE PREFERRED EMBODIMENTS

Figure 1:
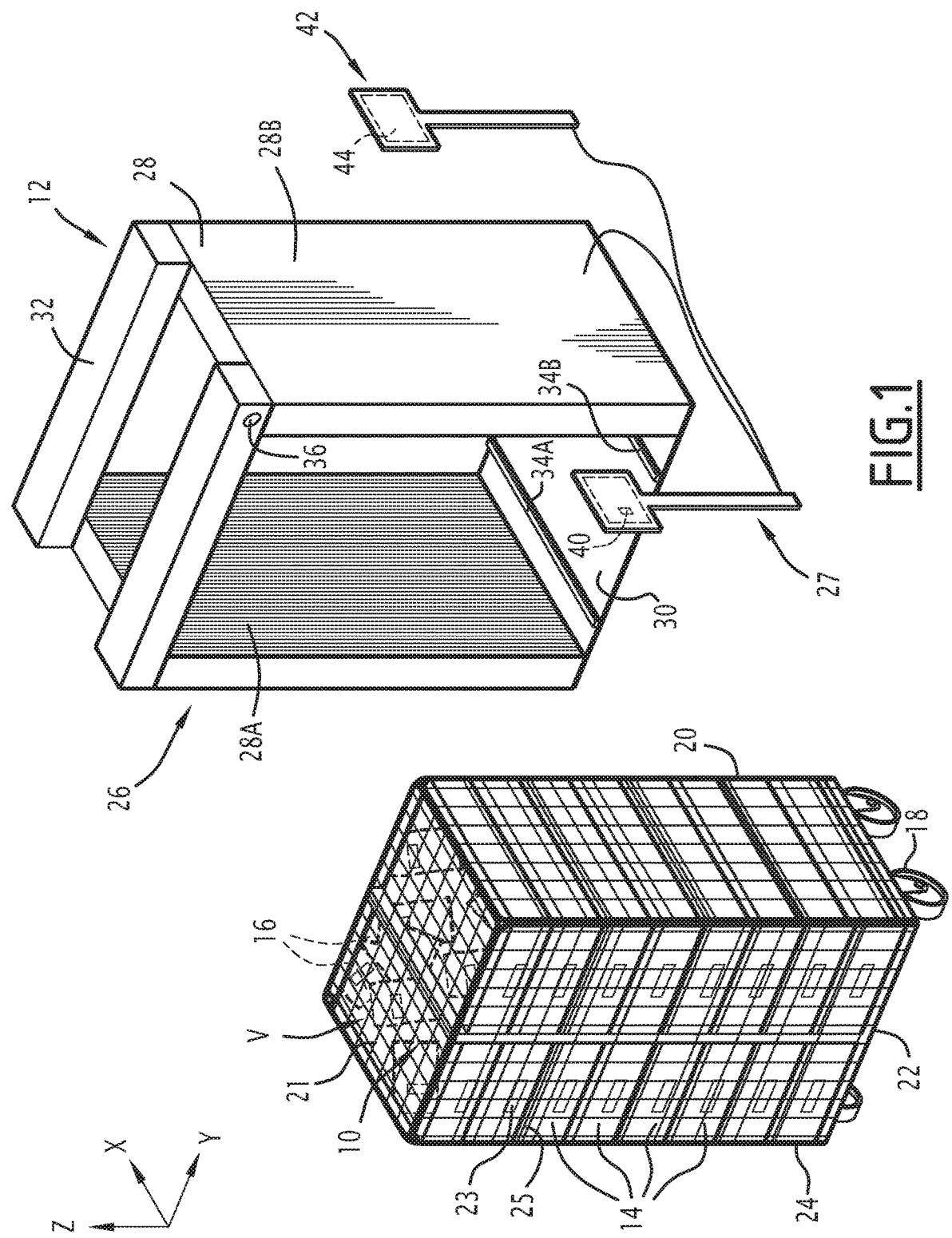
FIG. 1, a perspective view of a pallet of biological product containers on which an inventory must be carried out and a device for carrying out an inventory, the device including a gantry, FIG. 2, an illustration of the gantry of FIG. 1 seen along the direction of travel of the gantry, FIG. 3, an illustration of the gantry of FIG. 1 seen along the direction perpendicular to the direction of travel of the gantry, and FIG. 4, an illustration of another embodiment of a gantry, seen along a direction perpendicular to the direction of travel of the gantry.

A receptacle 10 and a device 12 for carrying out an inventory are shown in FIG. 1.

A receptacle is a transport assembly, often referred to using the generic term "roll". The receptacle 10 is intended to transport packages 14 from one location to another.

The receptacle 10 is able to accommodate a set of packages 14.

The number of packages 14 that the receptacle 10 is able to accommodate is greater than 22 packages.

According to one typical example, the number of packages 14 that the receptacle 10 is able to accommodate is equal to 22.

As an illustration, sixteen packages 14 are shown in FIG. 1.

Each package 14 assumes the form of a parallelepiped box.

Each package 14 is made from cardboard or plastic.

Each package 14 is able to accommodate a plurality of containers 16, each container 16 including biological products.

Generally, the container 16 is any type of pouch intended to contain products whose use is subject to strict storage constraints.

In one embodiment, the containers 16 are pouches containing biological products such as blood products (pouches of primary blood, plasma, platelets, red blood cells, etc.) or cellular engineering products (human or animal cells, in particular human or animal stem cells, products from human or animal cells).

In another embodiment, the containers 16 are drug pouches or therapeutic preparation pouches containing one or more active ingredients or medicaments, such as chemotherapy pouches (generally containing a solute and one or more chemotherapy active ingredients).

More generally, the container 16 is able to contain any product designed to be infused in a patient (human or animal).

According to the considered example, each container 16 is a pouch intended, in the present case, to contain plasma.

In a known manner, such a container 16 is a tight plasma container made from a breathable plastic material allowing metabolism, of the PVC (polyvinyl chloride), polycarbonate or PEG (polyethylene glycol) type.

The container 16 includes tubings that are sealed, for example by welding. These tubings were used, before sealing, to insert the plasma into the container 16.

An adhesive label is adhered onto an outer face of the package 14. This adhesive label includes a wireless communication chip.

Each chip corresponds to a unique identifier.

According to the proposed example, the wireless communication chip is an RFID chip.

The RFID chip includes a radiofrequency antenna, a memory and optionally a microprocessor.

The memory of each chip for example comprises the following information: the unique identifier, a package number, in order number and/or control data.

The device 12 is capable of carrying out an inventory of the content of a receptacle 10, i.e., packages 14 and/or containers 16 contained in each package.

In the embodiment shown in FIG. 1, the receptacle 10 is a cabinet with metal grating.

The receptacle 10 includes casters 18 and walls 20.

The casters 18 allow an operator to push the receptacle 10 to transported from one place to another. The receptacle is able to be moved.

According to the example of FIG. 1, the receptacle includes four casters 18 in contact with the ground. Only three casters 18 are visible, the last caster 18 forming a rectangle with the visible casters 18.

The plurality of walls 20 defines an inner volume V in which the packages 14 are intended to be located.

In the particular case of FIG. 1, the receptacle 10 includes at least six walls 20, namely a support wall 22, an upper wall 21 and three transverse walls 24, and a double front wall 23.

The receptacle 10 then forms a cage made up of metal grates.

The double door 23 is configured to open so as to allow filling of the receptacle 10 by packages 14.

The support wall 22 is intended to support the packages 14.

Each door 20 is formed by a metal grate.

The receptacle 10 further includes an inner wall and a plurality of racks 25, for example ten racks, delimiting compartments in the inner volume, each compartment being intended to receive a package 14.

The receptacle 10 is empty when the inner volume V has no packages 14, while the receptacle 10 is full when the entire inner volume V is filled with packages 14.

When the receptacle 10 is full, the receptacle 10 is heavy, typically with a weight greater than 200 kg. As a result, the full receptacle 10 is difficult for an operator to transport.

Alternatively, the receptacle 10 comprises a pallet forming a support wall and is moved using a pallet truck or a stacker, the casters of the pallet truck or the stacker then being considered casters of the receptacle. The number of packages 14 that the pallet 10 is able to accommodate is equal to 44 packages.

Alternatively, the receptacle 10 is a caddy including five walls, namely a support wall and four transverse walls, and casters. Each wall is formed by a metal grate.

The caddy has a height of less than or equal to 1.20 meters. The containers 16 are placed directly in the inner volume V defined by the caddy, without being accommodated in packages.

The device 12 includes a gantry 26 and at least one control terminal 27.

The gantry 26 includes two reading panels 28 resting on a floor 30.

The floor 30 is the floor of a location where the gantry is installed or is formed by a lower part of the gantry.

A direction of travel is defined for the gantry 26. The direction of travel is symbolized by an axis X in FIG. 1.

A first transverse direction is also defined corresponding to the direction perpendicular to the lower part 30. The first transverse direction is symbolized by an axis Z in FIG. 1.

A second transverse direction is defined as a direction perpendicular to the direction of travel for the gantry 26 and perpendicular to the first transverse direction. The second transverse direction is symbolized by an axis Y in FIG. 1.

In the illustrated embodiment, the gantry 26 comprises a roof 32. The roof 32 for example comprises two beams extending along the second transverse direction and connecting the two reading panels 28.

To clarify the remarks, the first reading panel is referenced 28A hereinafter, while the second reading panel is referenced 28B.

The first reading panel 28A assumes the form of a rhomb.

The first reading panel 28A has a first dimension along the second transverse direction Y, a second dimension along the first transverse dimension Z and a third dimension along the direction of travel X.

As shown in FIG. 2, the first dimension is denoted e1. The first dimension e1 corresponds to the thickness.

The first dimension e1 is between 200 mm and 400 mm (millimeters).

As shown in FIGS. 2 and 3, the second dimension is denoted e2. The second dimension e2 corresponds to the height The second dimension e2 is between 2000 mm and 3000 mm.

As shown in FIG. 3, the third dimension is denoted e3. The third dimension e3 corresponds to the depth.

The third dimension e3 is between 1000 mm and 2000 mm.

The first reading panel 28A includes a plurality of antennas A1 and A2.

As shown in FIG. 3, the first reading panel 28A includes two antennas A1 and A2.

The antennas A1 and A2 are placed next to one another in the first reading panel 28A.

The antennas A1 and A2 are spaced apart by a distance of between 50 mm and 150 mm.

Each antenna A1 and A2 is formed by a rectangular loop having rounded corners and characterized by a height, along the first transverse direction, and a width, along the direction of travel.

Each antenna A1 and A2 has a height of between 1500 mm and 2500 mm and a width of between 400 mm and 600 mm.

The antennas A1 and A2 have the same width and length and can be superimposed by translation along the direction of travel X.

Each antenna has an outgoing strand and an incoming strand.

Each antenna A1, A2 further comprises a switching and tuning card.

On the one hand, the card is provided for switching, i.e., using two mechanical electromechanical relays for connecting and/or disconnecting the antenna. Thus, one relay is connected to the outgoing strand of the antenna or disconnected, and the other relay is connected to the incoming strand of the antenna or disconnected.

On the other hand, the card is provided for tuning, i.e., adapting the impedance of the antenna to about $(50+j_0)$ ohms, $j_0$ being a complex value chosen to respect the tuning conditions explained hereinafter and to provide equilibration.

If the antenna does not have a tuned impedance, then part of the power leaves toward the source, which here is also the reader connected to the antennas. The power leaving toward the source is lost and may disrupt the reader.

The desired impedance verifies the following condition: $Za=Zs^*$ with $Za$ the impedance of the antenna and $Zs^*$ the complex conjugate of the impedance of the source. Here, the source has an impedance equal to $50+0\,j$ ohms, therefore the desired impedance of the antenna is $50+0\,j$ and $j_0=0\,j$ ohm.

Balancing is the minimization of the common mode current on a coaxial cable connecting the reader and the antenna.

The presence of metal, for example a receptacle 10 comprising a metal grating, in the field of the antenna affects the impedance of the antenna, therefore the performance of the antenna.

The closer the impedance is to $50+0\,j$ ohms, the better the performance of the reading panels will be. A first of the two antennas is tuned in free field, i.e., in the absence of metal between the reading panels 28A, 28B, and the second antenna is tuned near metal, for example from the cabinet or the metal grating caddy. The presence of two antennas thus makes it possible to obtain satisfactory performances in the presence of a receptacle with metal grating, but also without metal grating The same remarks as for the first reading panel 28A apply for the second reading panel 28B.

In particular, the second reading panel 28B includes two antennas B1 and B2.

The antennas A1, A2 of the first reading panel 28A are able to be superimposed with the antennas B1, B2 of the second reading panel 28B by translation along the second direction of travel Y.

An antenna A1 and A2 of the first reading panel 28A is associated bijectively with an antenna B1 and B2 of the second reading panel 28B, to form pairs of antennas.

Thus, the first antenna A1 of the first reading panel 28A and the first antenna B1 of the second reading panel 28B are associated to form a first pair of antennas, while the second antenna A2 of the first reading panel 28A and the second antenna B2 of the second reading panel 28B are associated to form a second pair of antennas.

The pairs of antennas are capable of reading RFID chips, in particular the RFID chips circulating in the gantry 10.

As a result, the panels 28A and 28B are described as being "reading panels" due to their ability to read RFID chips.

According to the example of FIG. 1, the two reading panels 28A and 28B face one another.

A first distance D1 is defined as the distance between the two reading panels 28A and 28B. The first distance D1 is the distance along the second transverse direction Y.

The first distance D1 is greater than or equal to 1000 mm.

The first distance D1 is less than or equal to 1700 mm.

According to one particular example, the floor 30 includes two guide members 34A and 34B.

Each guide member 34A and 34B is positioned at a second distance D2 from a respective reading panel 28A and 28B. The second distance D2 is the distance along the second transverse direction Y.

The second distance D2 was chosen experimentally by the applicant so that the antennas A1, A2, B1 and B2 can read the RFID labels.

Additionally, the second distance D2 is between 5 cm and 20 cm.

Alternatively, the movement of the receptacle 10 is carried out such that the distance between the receptacle 10 and one of the reading panels 28A, 28B is less than 10 cm. In this context, the distance is measured as the distance between the end of the receptacle 10 closest to a reading panel 28A or 28B.

Preferably, the distance between the receptacle 10 and one of the reading panels 28A, 28B is less than 5 cm.

Each guide member 34A and 34B assumes the form of a rail extending along the direction of travel X.

The cooperation between the casters 18 of a receptacle 10 manipulated by an operator and one of the guide members 34A and 34B ensures that the distance between the radiofrequency antennas of the labels and the corresponding reading panel 34A and 34B is less than 10 cm.

The gantry 26 further comprises an indicator 36. The indicator 36 indicates whether the gantry 26 is able to accommodate the passage of a receptacle.

The indicator 36 is for example a lighted signal that is green if the circulation of a receptacle in the gantry is authorized, white if the reading panels 28A, 28B are in the process of reading chips and red otherwise.

The control terminal 27 comprises a controller 40 and a man-machine interface 42. The controller 40 is able to control each antenna A1, A2, B1 and B2.

In particular, the controller 40 is able to inject controlled currents according to a control law specific to each antenna A1, A2, B1 and B2.

According to the present example, the controller 40 is able to apply a first control law for the currents ensuring that each pair of antennas A1 and B1 on the one hand and A2 and B2 on the other hand works alternatively in the so-called Helmholtz configuration. In such a primary control law, a same phase current is injected into each antenna A1 and B1 of the first pair of antennas, then another current of equal value is injected into each antenna A2 and B2 of the second pair of antennas.

Each current value is maintained during a period of time depending on a number of labels read by the reading panels 28A, 28B.

The man-machine interface 42 is able to display information.

The man-machine interface 42 for example comprises a screen 44 on each side of the gantry 26 along the direction of travel X, the information being displayed on both screens or on one selected screen. Thus, an operator is able to obtain the information whether he is on one side or the other of the gantry.

The man-machine interface 42 is able to display general information on the reception, anomalies or control information.

According to the present case, the screen is touch-sensitive such that the operator is able to interact with the gantry, for example, by indicating an order number or validating the displayed information. The touch-sensitive screen is compatible with gloves.

According to another example, the screen has buttons.

Alternatively, the man-machine interface 42 comprises only one screen on a single side of the gantry along the direction of travel X.

The controller 40 is for example integrated into one of the screens 44 of the man-machine interface 42.

The operation of the device 10 is now described in reference to a method for carrying out an inventory of a plurality of containers 16.

The method comprises a step for providing the device 12 and a step for providing a receptacle 10 comprising the plurality of containers 16 for which an inventory must be carried out.

The plurality of containers 16 is distributed into packages 14, as previously described.

The monitoring is for example done on the package scale.

The method also includes a step for moving the receptacle 10 in order to cross the gantry 26 in the direction of travel X.

In one embodiment, at least one caster 18 of the receptacle 10 cooperates with a guide member 34A, 34B during the movement.

The step for moving the receptacle 10 is carried out while the indicator 36 authorizes the circulation of a receptacle in the gantry.

For example, according to one particular example, a caster 18 is placed in contact in a guide member 34A, 34B, then the operator pushes the receptacle 10 such that the caster 18 remains in contact with the guide member 34A, 34B all throughout the movement.

According to another example, in which the receptacle comprises a pallet moved using a pallet truck or a stacker, the pallet truck is moved between the guide members 34A, 34B.

The method comprises a step for detecting a passage of a receptacle 10 using at least one detection sensor, for example, laser sensors or a weight sensor. The passage of a receptacle is detected at each end of the gantry 26 along the direction of travel X.

When the passage of a receptacle is detected, then a step for reading wireless communication chips is carried out by at least one of the reading panels 28A, 28B during the movement of the receptacle 10.

For example, the controller 40 carries out the first command law, which consists alternatively of applying a current on the first pair of antennas, then a current on the second pair of antennas.

The lighted signal of the indicator 36 then becomes white.

The reading step is carried out dynamically or statically, i.e., the receptacle moves or is immobilized between the reading panels 28A, 28B during the reading step. The receptacle moves, for example, at less than 5 km/h.

It has been shown by the applicant that such a first control law makes it possible, despite the presence of materials of the packages 16 and metal of the receptacle 10, to detect any wireless communication chips located between the reading panels 28A, 28B.

In one embodiment, the reading step is stopped after a determined duration and configured by the operator bringing the receptacle or beforehand. The lighted signal of the indicator 36 then becomes green or red, depending on the case.

If, during the reading step, no chip has been identified, then the man-machine interface 42 for example proposes to start a new reading step.

The control terminal 27 has, in memory, the list of chips detected by the gantry 26 and the corresponding packages and/or containers owing to the respective unique identifier.

The man-machine interface 42 displays information on the detected labels, the monitoring of the containers or the reception.

The man-machine interface 42 for example displays one or several of the following pieces of information: the number of chips detected, the identifiers of the detected chips, the corresponding containers and/or the category of the product contained in the containers in the package, for example, the quality of the plasma.

A verification step is performed.

During the verification step, the compliance of the receptacle 10 to be received is verified. For example, if the number of packages is equal to an expected number and if the nature of the product contained in the containers corresponds to that to be received, then the reception is validated and a message confirming reception is displayed on the man-machine interface; otherwise, a corresponding message is displayed on the man-machine interface 42.

If the number of packages is lower than the expected number, the operator for example has the choice of validating the number, the rest of the packages remaining to be received later, starting a new reading step or manually entering chips that were not detected.

The man-machine interface 42 optionally displays additional information. The information for example relates to an anomaly or an inspection to be done.

This information is for example one or more of the following pieces of information:
 past and/or planned itinerary of the containers and/or packages,
 an error because the packages are of several quality groups,
 an error related to a difference between the number of detected RFID chips and the weight or the maximum contents of the receptacle,
 an error related to an unknown RID chip, and/or
 an error related to a detected RFID chip corresponding to a package comprising at least one container for which monitoring is not available or was not done correctly, for example if a plasma container is expired or was not kept at an appropriate temperature.

In one embodiment, the method comprises a reconciliation step, during which the detected RFID chips are associated with a container in which the associated containers are expected to be stored. Said container is for example the receptacle 10 if the receptacle 10 is stored directly.

The man-machine interface 42 displays whether the method comprises such a reconciliation step.

If at least one of the detected RFID chips has already been associated with another container, then an error message is displayed on the man-machine interface 42. The man-machine interface 42 is then able to indicate the affected package(s) such that an operator can remove them from the receptacle 10 and place them on the provided container. Alternatively, after validation, said RFID chip will be associated with the new container.

Then, the list of detected RFID chips is for example sent to a central management system for a stock whose inputs and/or outputs are managed by the gantry. The transmission is for example done by Ethernet link to a dedicated server.

After transmission, the list is deleted from the controller 40 of the gantry.

Additionally or alternatively, an adhesive label, as described in light of the packages 14, is adhered on an outer face of each container 16. The gantry 26 is then provided to identify the different containers 16, including those present in a package 14, on the receptacle 10.

Additionally, an adhesive label, as described in light of the packages 14, is adhered on the receptacle 10. The gantry 26 is then provided to identify the receptacle 10.

In these embodiments, an operating mode of the gantry 26 is provided in which the gantry 26 only processes the chips corresponding to one object type, for example, the containers 16, the packages 14 or the receptacle 10.

The method for carrying out an inventory of a plurality of biological product containers is thus fast to carry out.

More generally, this makes it possible to save time upon receiving packages 16.

The direction of travel of the gantry is indifferent, such that the operator can choose the most appropriate direction for the situation. Typically, the operator chooses the direction of travel minimizing the distance to be covered by pushing the receptacle 10.

This also guarantees less unpleasant stresses for the operator.

According to one embodiment, the gantry 26 further comprises a sensor provided to read barcodes, the gantry 26 being able to operate in a downgraded mode in which an operator uses said sensor to scan a barcode present on each package label and/or container or uses the man-machine interface 24 to enter respective numbers corresponding to the barcodes.

According to one embodiment, the movement and reading steps are carried out in an enclosure with a controlled atmosphere.

For example, the enclosure has a controlled temperature, typically between 0° C. and 5° C., more particularly equal to +4° C.

In such cases, the temperature gain obtained by using the device 12 further makes it possible to better respect the legislative provisions seeking to guarantee better conservation of the biological products of each container 16.

Alternatively, a control law other than the first control law is used.

For example, instead of applying a phase current in each pair of antennas, a phase-shift is introduced between the two currents.

When the phase shift is 180°, a so-called magnetic mirror configuration is obtained allowing a reading of an RFID chip that would be oriented so as to be normal to the direction of travel X.

When the phase shift is 90°, an alternation is obtained between the so-called Helmholtz configuration and the so-called magnetic mirror configuration. This in particular makes it possible to read the labels, irrespective of the direction of the labels.

In this alternative, the method for carrying out an inventory of a plurality of biological product containers is also carried out more quickly than during an inventory by scanning barcodes.

In an alternative shown in FIG. 4, each reading panel 28A, 28B includes a single antenna A, B.

Each antenna A, B is formed by a loop. Each antenna A, B is for example in the form of a rectangular loop having rounded corners and characterized by a height, along the first transverse direction Z, and a width, along the direction of travel X.

According to the illustrated example, the loop has an opening in the middle of an upper side along its width.

The height is for example between 1500 mm and 2500 mm, and its width is for example between 750 mm and 1250 mm.

The antennas A, B of the two reading panels 28A, 28B have the same dimensions and can be superimposed by translation along the second transverse direction Y.

Each antenna A, B comprises two switched tuning circuits making it possible to operate each antenna selectively according to two different operating modes: a "free field"

mode and a "metal proximity" mode, similarly to the two antennas of a same reading panel in the previous embodiment.

The antenna A of the first reading panel 28A is associated bijectively with the antenna B of the second reading panel 28B, to form a pair of antennas.

The pair of antennas A, B is capable of reading RFID chips, in particular the RFID chips circulating in the gantry 10, similarly to the embodiment previously described.

The controller 40 is able to control each antenna. In particular, the controller 40 is able to inject controlled currents according to a control law specific to each antenna.

The implementation method is similar to what was described previously, and the same advantages are obtained.

The invention claimed is:

1. A method for carrying out an inventory of a plurality of biological product containers, one or more of each of the biological product containers and a package including the biological product containers being provided with an identification label with a wireless communication chip, the method comprising:
   providing a device configured to carry out the inventory of the plurality of biological product containers, the device including a gantry defining a direction of travel, the gantry comprising two reading panels, each of the reading panels including a plurality of antennas configured to read the wireless communication chip, the plurality of antennas being disposed next to one another;
   providing a receptacle configured to be moved, the receptacle bearing the plurality of biological product containers for which the inventory is to be carried out; and
   reading, by at least one of the reading panels, the wireless communication chip by successively supplying the plurality of antennas with current during a predefined period of time.

2. The method according to claim 1, further comprising moving the receptacle in order to cross the gantry in the direction of travel, the reading being carried out during the movement of the receptacle.

3. The method according to claim 2, wherein the gantry further comprises a floor including at least one guide member extending along the direction of travel, each guide member being associated with a respective reading panel and being arranged at a distance smaller than 20 centimeters from a respective reading panel along a direction transverse to the direction of travel, each receptacle comprising a plurality of casters, at least one caster being configured to cooperate with at least one guide member.

4. The method according to claim 2, wherein the moving and the reading are carried out in an enclosure with a controlled atmosphere.

5. The method according to claim 1, wherein the receptacle comprises at least one wall formed by a metal grating.

6. The method according to claim 1, wherein one of the antennas of the reading panels is associated bijectively with one of the antennas of another of the reading panels to form pairs of antennas.

7. The method according to claim 6, wherein the current applied in each pair of antennas respects one of the following conditions: being in phase, being phase-shifted by 90°, and being phase-shifted by 180°.

8. The method according to claim 1, wherein each of the reading panels includes only two antennas.

9. A device for carrying out an inventory of a plurality of biological product containers, one or more of each of the biological product containers and a package including the biological product containers being provided with an identification label with a wireless communication chip, the plurality of containers for which the inventory is to be carried out being part of a receptacle, the device comprising:
   a gantry defining a direction of travel, the gantry comprising two reading panels, each of the reading panels including a plurality of antennas configured to read the wireless communication chip, the plurality of antennas being disposed next to one another; and
   a control terminal comprising a controller configured to command the antennas to read at least one of the reading panels of the wireless communication chip by successively supplying the plurality of antennas with current during a predefined period of time.

10. The device according to claim 9, wherein the controller is configured to command the antennas to carry out the reading during the movement of the receptacle to traverse the gantry along the direction of travel.

11. A method for conducting an inventory of a plurality of biological product containers, the method comprising:
   providing one or more of the biological product containers and at least one package comprising the biological product containers, the one or more of the containers and the at least one package being provided with an identification tag comprising a wireless communication chip;
   providing a device including a portal comprising two reading panels, each of the reading panels including a plurality of antennas configured to read the wireless communication chip, the plurality of antennas being disposed next to one another; and
   reading, by at least one of the reading panels, the wireless communication chip by successively supplying the plurality of antennas with current during a predefined period of time.

* * * * *